United States Patent
Inagaki

(10) Patent No.: US 9,952,120 B2
(45) Date of Patent: Apr. 24, 2018

(54) SENSOR CONTROL DEVICE AND SENSOR CONTROL SYSTEM

(71) Applicant: NGK SPARK PLUG CO., LTD., Nagoya-shi, Aichi (JP)

(72) Inventor: Hiroshi Inagaki, Komaki (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 1095 days.

(21) Appl. No.: 13/680,288

(22) Filed: Nov. 19, 2012

(65) Prior Publication Data

US 2013/0131997 A1    May 23, 2013

(30) Foreign Application Priority Data

Nov. 17, 2011 (JP) .................................. 2011-251701
Sep. 28, 2012 (JP) .................................. 2012-217061

(51) Int. Cl.

| G01M 15/04 | (2006.01) |
| G01N 27/406 | (2006.01) |
| G01N 37/00 | (2006.01) |
| G06F 15/00 | (2006.01) |
| F02D 41/24 | (2006.01) |

(Continued)

(52) U.S. Cl.
CPC ......... *G01M 15/042* (2013.01); *F02D 41/144* (2013.01); *F02D 41/1458* (2013.01); *F02D 41/1494* (2013.01); *F02D 41/2474* (2013.01); *G01N 27/4065* (2013.01);

(Continued)

(58) Field of Classification Search
None
See application file for complete search history.

(56) References Cited

U.S. PATENT DOCUMENTS

| 4,727,849 A | 3/1988 | Nishida et al. |
| 4,836,174 A | 6/1989 | Chujo et al. |
| 2011/0166816 A1* | 7/2011 | Ishiguro et al. ............. 702/104 |

FOREIGN PATENT DOCUMENTS

| EP | 1333171 A1 | 8/2003 |
| EP | 1333171 B1 | 4/2005 |

(Continued)

OTHER PUBLICATIONS

Communication from the Japanese Patent Office dated Mar. 11, 2014, in a counterpart Japanese application No. 2012-217061.

*Primary Examiner* — John Kuan
(74) *Attorney, Agent, or Firm* — Sughrue Mion, PLLC

(57) ABSTRACT

A sensor control device for connection to an oxygen sensor including a sensing element that measures oxygen concentration in an intake atmosphere of an internal combustion engine and a heater that heats the sensing element, including a detection unit that detects an output signal corresponding to the oxygen concentration output from the sensing element and a calculation unit that calculates a compensation coefficient of the output signal that is used when calculating the oxygen concentration. The calculation unit collects compensation information used in calculating the compensation coefficient when the internal combustion engine is in operation and in a specific operation state in which the oxygen concentration in the intake atmosphere is subject to estimation. Also disclosed is a sensor control system which includes an oxygen sensor and the sensor control device.

4 Claims, 5 Drawing Sheets

(51) Int. Cl.
*F02D 41/14* (2006.01)
*F02D 41/00* (2006.01)
*F02D 41/08* (2006.01)

(52) U.S. Cl.
CPC ............ *G01N 37/00* (2013.01); *G06F 15/00* (2013.01); *F02D 41/0055* (2013.01); *F02D 41/08* (2013.01)

(56) References Cited

FOREIGN PATENT DOCUMENTS

| | | | |
|---|---|---|---|
| JP | 63-227948 | A | 9/1988 |
| JP | 2-221647 | A | 9/1990 |
| JP | 02221647 | A * | 9/1990 |
| JP | 10-176577 | A | 6/1998 |
| JP | 2003-214245 | A | 7/2003 |
| JP | 2004-19629 | A | 1/2004 |
| JP | 2011-021567 | A | 2/2011 |

* cited by examiner

SENSOR CONTROL DEVICE AND SENSOR CONTROL SYSTEM

BACKGROUND OF THE INVENTION

1. Field of the Invention

The present invention relates to a sensor control device and a sensor control system that measures, for example, the concentration of a specific component in an object measurement gas such as an intake charge mixture of an internal combustion engine and that is suitable for use in compensating an output signal of an oxygen sensor.

2. Description of the Related Art

In an internal combustion engine in recent years, the control of an air-fuel ratio that is a ratio of fuel to intake air, and more specifically, the control of a ratio of fuel to oxygen included in the intake air is generally performed for the purpose of improving fuel economy and reducing harmful substances included in exhaust gas. When performing this control, it is necessary to measure the volume of the intake air. For example, a method is known using an air mass flow sensor for measuring the volume of the intake air. The air mass flow sensor is used in an internal combustion engine equipped with an intake throttle valve and may be used to measure the cylinder air intake volume, which changes according to an operation state.

On the other hand, an intake throttle valve is not provided in a diesel engine, a direct-injection gasoline engine, and the like, and the volume of cylinder air intake volume is basically constant. Moreover, in a diesel engine having an exhaust gas recirculation device (hereinafter referred to as an "EGR device") for recirculating a part of the post-combustion exhaust gas into the intake air, the ratio of oxygen included in the intake air changes due to an amount of recirculating exhaust gas (hereinafter referred to as "EGR amount"). In other words, the amount of cylinder oxygen intake changes.

In this case, the air-fuel ratio is difficult to precisely control using only the air mass flow sensor described above. That is, in control of air-fuel ratio using only an air mass flow sensor, the amount of cylinder oxygen intake is calculated assuming that the ratio of oxygen included in the intake air, for example, is the same as the ratio of oxygen included in the atmosphere. The amount of cylinder oxygen intake may not be accurately calculated because the ratio of oxygen included in the intake air changes in an internal combustion engine equipped with an EGR device.

To solve the above described problems, an oxygen sensor that measures oxygen concentration included in the intake air is used, and a technique that calculates an amount of cylinder oxygen intake has been proposed (see, for example, JP-A-H02-221647). In this technique, an amount of cylinder oxygen intake is calculated by measuring the volume of cylinder air intake with the air mass flow sensor and further measuring the oxygen concentration of the intake air with the oxygen sensor. For control of the air-fuel ratio, a feed-forward control is considered to provide good results in which an amount of fuel injected into the cylinder or an intake port is controlled according to the amount of oxygen that is calculated as described above.

[Patent Document 1] JP-A-H02-221647

3. Problems to be Solved by the Invention

It is known that it is necessary to compensate for a change in an output value resulting from, for example, deterioration in the oxygen sensor in a case where the oxygen sensor is used as described above. Especially, in a case where the oxygen sensor is arranged only in an intake system, high oxygen sensor accuracy is required. Further, the necessity for compensation is increased, as compared to the case where oxygen sensors are arranged in the intake system and a non-intake system. For this reason, the technique, disclosed in JP-A-H02-221647 also compensates an output value of the oxygen sensor after the internal combustion engine stops.

However, electric power is always consumed when compensating the output value of the oxygen sensor, and in a case of a vehicle, the electric power is supplied from a mounted battery. When the electric power of the battery is not sufficient in the case where the compensation is performed after the internal combustion engine stops, as disclosed in JP-A-H02-221647, there is a concern that the compensation may not be performed in an accurate state. More particularly, this might be the case where a heater of the oxygen sensor may not be sufficiently driven, or the case where a temperature of the sensing element may not be precisely controlled. Furthermore, even in a case where the compensation is performed, there is a concern that the battery is easily drained because the electric power of the battery is consumed.

SUMMARY OF THE INVENTION

It is therefore an object of the present invention to provide a sensor control device and a sensor control system that are capable of suppressing deterioration in measurement accuracy of an oxygen sensor equipped with a heater while suppressing consumption of electric power of a battery installed together with an internal combustion engine.

The above object of the invention has been achieved, in a first aspect (1), by providing a sensor control device for connection to an oxygen sensor including a sensing element that measures oxygen concentration in an intake atmosphere of an internal combustion engine and a heater that heats the sensing element, the sensor control device comprising: a detection unit that detects an output signal corresponding to the oxygen concentration output from the sensing element; and a calculation unit that calculates a compensation coefficient of the output signal used for calculating the oxygen concentration, wherein the calculation unit collects compensation information used in calculating the compensation coefficient when the internal combustion engine is in operation and in a specific operation state in which the oxygen concentration in the intake atmosphere is subject to estimation.

According to the sensor control device of the present invention, the collection of compensation information used to calculate a compensation coefficient is performed when the internal combustion engine is in operation and is in a specific operation state where oxygen concentration in the intake atmosphere is subject to estimation. Accordingly, the compensation coefficient used to compensate an output signal of a sensing element based on the compensation information may be calculated and updated. Thus, even though deviation occurs due to, for example, deterioration in the sensing element, in a correspondence relationship between a value of the output signal of the sensing element and the oxygen concentration in the intake atmosphere, the deviation in the corresponding correspondence relationship may be resolved by compensating the output signal using the compensation coefficient calculated in the calculation unit. In addition, in the present invention, the calculation unit collects the compensation information used to calculate the compensation coefficient while the internal combustion engine is in operation, as described above. The timing at which the calculation unit calculates and updates the compensation coefficient of the output signal may be at a time when the internal combustion engine is in operation and may be at the time when the internal combustion engine is in a non-operation state. The timing is not particularly limited.

Furthermore, in the sensor control device of the present invention, because the calculation unit collects the compensation information described above while a generator is driven by the internal combustion engine and the battery installed together with the internal combustion engine is charged, the consumption of the electric power of the battery may be suppressed, as compared to the case where the compensation information is collected while the internal combustion engine is stopped. In other words, a specific operation state in which the oxygen concentration of the intake atmosphere is subject to estimation is a state in which the oxygen concentration stored in advance in the calculation unit and the oxygen concentration in the intake atmosphere are the same. Furthermore, the state in which the internal combustion engine is in operation, for example, refers to the state in which the internal combustion engine is driven without the key being OFF (including an idle operation state). Further, if the internal combustion engine is driven for a certain period, this state is included in the state in which the internal combustion engine is in operation, regardless of whether or not a vehicle runs in a case where the internal combustion engine is mounted in the vehicle.

In a preferred embodiment (2) of the sensor control device (1) of the invention, the specific operation state is a state in which an opening degree of a control valve controlling an amount of recirculating exhaust gas, which is provided in an exhaust gas recirculation device that recirculates a part of the exhaust gas in the internal combustion engine into the intake atmosphere, is less than a predetermined opening degree, the oxygen concentration in the intake atmosphere in a case where the opening degree of the control valve is less than the predetermined opening degree is stored in advance in the calculation unit, and the calculation unit collects the compensation information when the opening degree of the control valve is less than the predetermined opening degree.

In this manner, by defining the specific operation state as a state in which an opening degree of a control valve of an exhaust gas recirculation device is less than a predetermined opening degree, the calculation may be performed more accurately, based on a relationship between the oxygen concentration stored in advance in the calculation unit and the opening degree of the control valve. In other words, the compensation coefficient may be calculated based on the compensation information collected in a state in which the oxygen concentration stored in advance in the calculation unit and the oxygen concentration in the intake atmosphere match each other. At this point, the state in which the opening degree of the control valve is less than the predetermined opening degree exemplifies a state in which there is no need to substantially consider a change in the oxygen concentration in the intake atmosphere due to the recirculation of exhaust gas.

In another preferred embodiment (3) of the sensor control device (2), the specific operation state is such that the operation state of the internal combustion engine is in an idle operation state, the oxygen concentration in a case where the opening degree of the control valve is less than the predetermined opening degree and the internal combustion engine is in the idle operation state may be stored in advance in the calculation unit, and the calculation unit collects the compensation information when the internal combustion engine is in an idle operation state.

In this manner, by defining the specific operation state as a state in which the opening degree of the control valve of the exhaust gas recirculation device is less than the predetermined opening degree and further, as a state in which the internal combustion engine is in the idle operation state, the compensation coefficient may be calculated more accurately based on the oxygen concentration stored in advance in the calculation unit.

That is, in a case where the internal combustion engine is in idle operation, a flow volume of the intake atmosphere into the internal combustion engine is decreased, as compared to the case where the internal combustion engine is driven in a high-load condition. Then, in an area where the sensing element is arranged, a flow velocity of the intake atmosphere is decreased and further, a pressure of the intake atmosphere is close to atmospheric pressure. Generally, an output signal of the sensing element depends on the temperature of the sensing element, and further depends on the surrounding pressure. An amount of heat of the sensing element removed by the intake atmosphere is decreased, by lowering the flow velocity of the intake atmosphere, and thus the temperature is easy to control to a predetermined constant temperature and the output signal is readily stabilized. Similarly, by controlling the pressure around the sensing element to a predetermined constant pressure, that is, to a pressure near the atmospheric pressure, the output signal is easy to stabilize. In this manner, the calculation of a more accurate correction coefficient may be performed by collecting the compensation information after stabilizing the output signal.

Moreover, when the engine is idling, a load applied to the internal combustion engine is small. The amount of blow-by gas (that is, an exhaust gas leaking from, for example, a clearance between the cylinder and a piston of the internal combustion engine) is also small. When the blow-by gas is mixed into the intake atmosphere, an error results when estimating the oxygen concentration in the intake atmosphere. When collecting the compensation information while the internal combustion engine is idling, the influence of the blow-by gas is small. Thus a compensation coefficient with high accuracy may be calculated, for example, as compared to the case where compensation information is collected when the engine is operated under a high-load condition.

In addition, the "idle operation state" in the present invention refers to a state in which the engine revolves without outputting significant power. Specifically, the "idle operation state" refers to an operation state that meets any one of the following conditions: 1) an accelerator pedal is in approximately a no-load condition without being depressed (including a state in which a vehicle moves at a very slow speed caused by transmission of torque to wheels via a torque converter (i.e., a creep state), 2) an internal combustion engine is in a warming-up operation state, and 3) a gear shift lever of a vehicle is in a neutral state.

In yet another preferred embodiment (4) of the sensor control device (3), the calculation unit collects the compensation information when the idle operation state has continued for a predetermined period of time. In this manner, the compensation information can be collected under a condition where the output signal of the sensing element is more stable. Further, the compensation information can be collected under a condition where the amount of blow-by gas is very small. Accordingly, it is possible to calculate the compensation coefficient with higher accuracy.

In yet another preferred embodiment (5) of the sensor control device of any of (2) to (4) above, the oxygen concentration in the operation state where the opening degree of the control valve stored in advance in the calculation unit is less than the predetermined opening degree is the oxygen concentration in the intake atmosphere when the control valve is closed, and the calculation unit collects the compensation information when the control valve is closed.

In this manner, the compensation coefficient may be more accurately calculated by storing in advance the oxygen concentration in the intake atmosphere when the control valve of the exhaust gas recirculation device is closed, wherein the calculation unit collects the compensation information when the control valve described above is in a closed state. The state in which the control valve is in a closed state refers to a state in which an amount of recirculation exhaust gas is not present in the intake atmosphere, and refers to a state in which a passage through which a part of the exhaust gas is recirculated into the intake atmosphere is entirely blocked by the control valve. In other words, the concentration of the specific gas in the intake atmosphere is such that its concentration is estimated to be the same as that of the specific gas in the atmosphere. Thus, the concentration of the specific gas in the intake atmosphere in the state where the control valve is closed may be determined with increased accuracy, and the output signal may be compensated with increased accuracy as well.

In yet another preferred embodiment (6) of the sensor control device of any of (1) to (5) above, a basic value that is the output signal of the sensing element with respect to the oxygen concentration in the specific operation state is stored in advance in the calculation unit, and the calculation unit stores a plurality of the output signals detected in the specific state, calculates an average value of the plurality of the stored output signals, and updates the compensation coefficient in a case where a difference between the basic value stored in advance and the average value is greater than a predetermined value.

In this manner, by updating the compensation coefficient only in a case where a difference between a basic value and an average value deviates from a predetermined range, the risk that accuracy in measuring the oxygen concentration is decreased all the more due to excessive updates on the compensation coefficient may be reduced.

The above object of the invention has also been achieved, in a second aspect, by providing a sensor control system comprising: an oxygen sensor including, a sensing element that measures oxygen concentration in an intake atmosphere in an internal combustion engine, and a heater heating the sensing element; a state measurement unit that outputs a state signal corresponding to an operation state of the internal combustion engine; a determination unit that determines whether or not the internal combustion engine is in a specific operation state, based on the state signal; and the sensor control device according to the first aspect (1) above, wherein the calculation unit of the sensor control device collects the compensation information based on a determination result by the determination unit.

According to the sensor control system of the second aspect of the present invention, the deterioration in measurement accuracy of the oxygen sensor may be suppressed while suppressing the consumption of electric power of the battery installed together with the internal combustion engine. In addition, a signal that estimates the oxygen concentration in the intake atmosphere typical of the state signal according to the operation state in which the internal combustion engine is in operation, a signal that indicates the opening degree of the control valve controlling an amount of recirculating exhaust gas in the exhaust gas recirculation device, and a signal relating to the number of revolutions of the engine and the like exemplify various preferred embodiments of the sensor control system.

Advantages of the Invention

According to the sensor control device and sensor control system of the present invention, deterioration in measurement accuracy of an oxygen sensor equipped with a heater may be suppressed while suppressing the consumption of electric power of a battery installed together with the internal combustion engine. This is because the compensation coefficient is calculated based on compensation information collected when the internal combustion engine is in operation and in an operation state in which the oxygen concentration in the intake atmosphere is subject to estimation.

DESCRIPTION OF REFERENCE NUMERALS

Figure 1:
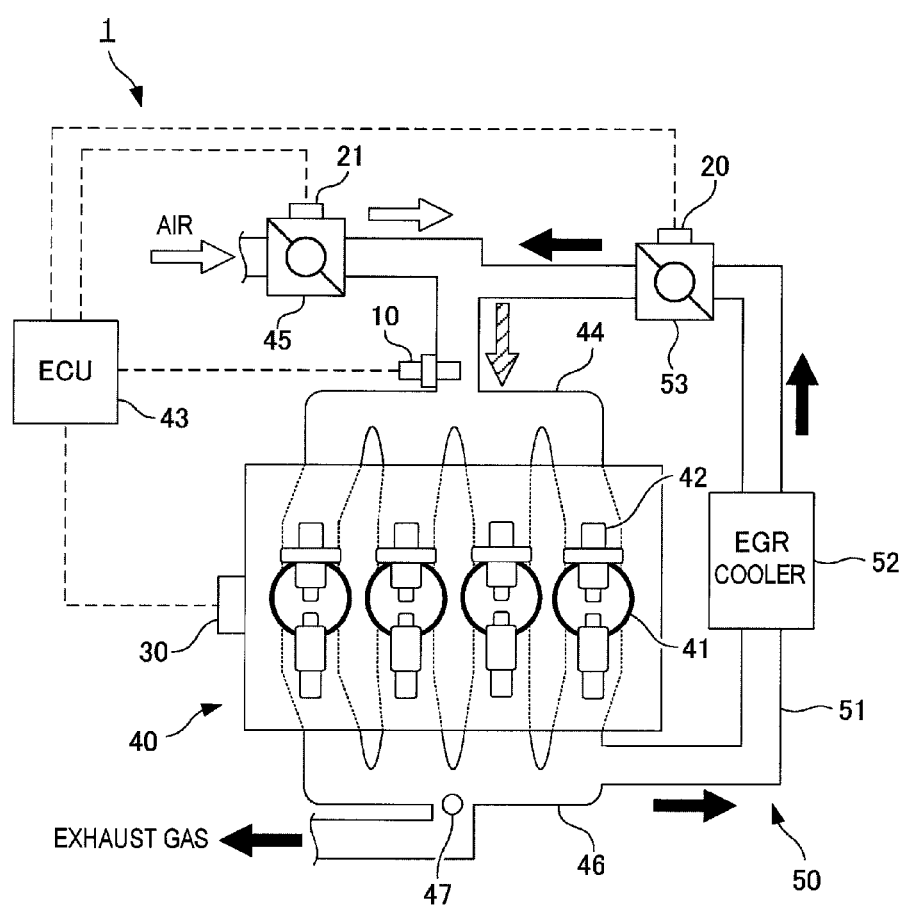
FIG. 1 is a schematic diagram of the entire configuration of a sensor control system according to a first embodiment of the present embodiment.

Reference numerals used to identify various features in the drawings include the following.
1, 101 Sensor control system
10, 110 oxygen sensor
11 sensing element
12, 112 oxygen sensor control unit (oxygen sensor control device)
13 detection unit
15 calculation unit
17 heater
20 opening-degree sensor (state measurement unit)
21 throttle opening-degree sensor (state measurement unit)
30 revolution-per-minute sensor (state measurement unit)
40 engine (internal combustion engine)
43 ECU (determination unit)
50 EGR device (exhaust gas recirculation device)
53 EGR valve (control valve)

DETAILED DESCRIPTION OF THE PREFERRED EMBODIMENTS

First Embodiment

A sensor control system according to a first embodiment of the present invention is described by reference to FIGS. 1 to 3. However, the present invention should not be construed as being limited thereto. FIG. 1 is a schematic diagram which describes the entire configuration of the sensor control system according to the present embodiment.

The sensor control system 1 of the present embodiment is provided in a diesel engine (hereinafter referred to as an "engine") 40 that is an internal combustion engine equipped with an EGR device (an exhaust gas recirculation device) 50. The sensor control system 1 performs calculation processing that acquires (calculates) the oxygen concentration in the intake atmosphere, based on an output signal Ip from an oxygen sensor 10 measuring oxygen concentration in an intake atmosphere and a compensation coefficient Ipcomp stored in an engine control unit 43.

Moreover, the sensor control system 1 compensates the compensation coefficient Ipcomp and controls a decrease in the accuracy of the oxygen concentration acquired by the calculation processing. This is in the case where the accuracy of the oxygen concentration acquired by the calculation processing decreases due to, for example, deterioration in a sensing element 11 constituting the oxygen sensor 10. Moreover, an influence due to deterioration in the sensing element 11 tends to become prominent after a vehicle equipped with the engine 40 runs from several thousand km to several ten thousand km, and thus an update on the compensation coefficient Ipcomp is not performed at all times.

The oxygen sensor 10, an EGR opening-degree sensor (a state measurement unit) 20 detecting an opening degree of an EGR valve 53 of the EGR device 50, a throttle opening-degree sensor (a state measurement unit) 21 detecting an opening degree of a throttle valve 45, and a revolution-per-minute sensor 30 (a state measurement unit) detecting the number of revolutions of the engine 40 per unit time are mainly provided in the sensor control system 1.

The oxygen sensor 10 is provided in a passage (in other words, an intake passage through which an intake charge mixture for a combustion chamber of the engine 40 is supplied) through which the intake atmosphere into the engine 40 flows, and is a sensor that measures the oxygen concentration in the intake atmosphere. More specifically, the oxygen sensor 10 is provided in an intake manifold 44 at a position after the flow of the air intake and an exhaust gas recirculated by the EGR device 50 are joined together. Moreover, the throttle valve 45 that controls a flow volume of air is provided in an area through which only air flows, in other words, in an upstream area, in the intake manifold 44.

Furthermore, multiple cylinders 41 where an air-fuel mixture of the intake atmosphere and a fuel burns, an injector 42 injecting the fuel into each cylinder 41, and the engine control unit 43 (hereinafter referred to as "ECU 43") controlling the engine 40 are provided in the engine 40. An example of the engine 40 equipped with the four cylinders 41 is illustrated in FIG. 1, but the number of the cylinders 41, with which the engine 40 is equipped, is not particularly limited.

In the engine 40, the intake manifold 44 described above is installed and an exhaust manifold 46 through which the exhaust gas flows after the air-fuel mixture in the cylinder 41 burns is installed. An exhaust oxygen sensor 47 that measures the oxygen concentration contained in the exhaust gas is arranged in the exhaust manifold 46.

An EGR passage 51 that connects to the exhaust manifold 46 and the intake manifold 44 to enable the recirculation of the exhaust gas from the exhaust manifold 46 to the intake manifold 44, an EGR cooler 52 that decreases a temperature of the exhaust gas recirculating through the EGR passage 51, and the EGR valve (a control valve) 53 that controls a flow volume of the exhaust gas recirculating through the EGR passage 51 are mainly provided in the EGR device 50.

Figure 2:
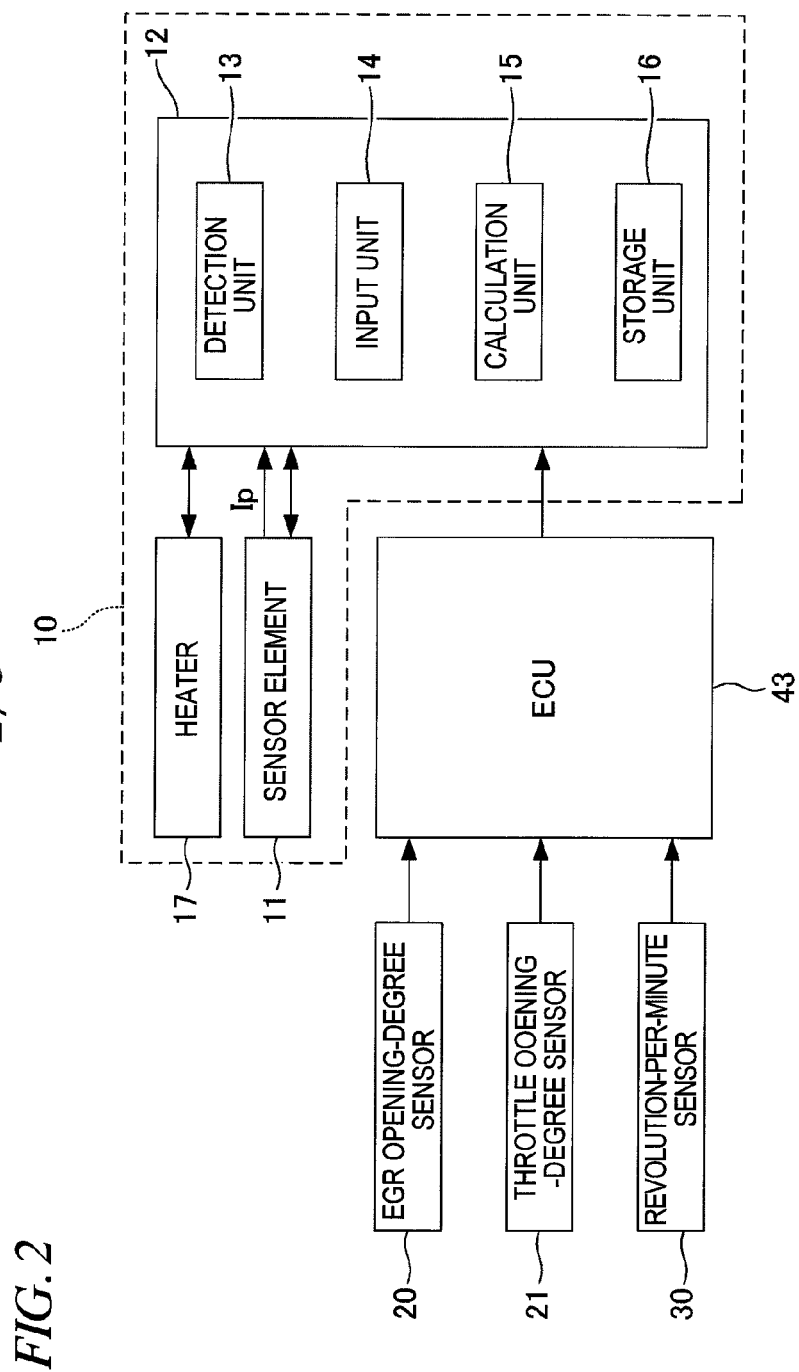
FIG. 2 is a block diagram of a configuration of the oxygen sensor shown in FIG. 1.

FIG. 2 is a block diagram of a configuration of the oxygen sensor 10 of FIG. 1.

As illustrated in FIG. 2, the sensing element 11 that measures the oxygen concentration in the intake atmosphere, a heater 17 that heats the sensing element 11, and an oxygen sensor control unit (an oxygen sensor control device) 12 that compensates the output signal Ip output from the sensing element 11 are mainly provided in the oxygen sensor 10.

In the sensing element 11, the output signal Ip changes linearly according to the oxygen concentration in the intake atmosphere. The sensing element has a two-cell type configuration in which an oxygen pump cell and an electromotive force detection cell, with a pair of electrodes being set in each cell, are laminated on the front and back surfaces of a solid electrolyte layer having oxygen ion conductivity, and containing zirconia as a main ingredient. Since the two-cell type sensing element 11 is well known, a detailed description is omitted, but an outline description thereof is as follows. The two cells are laminated by interposing a spacer layer on which a measurement chamber with a recess in the middle and a porous diffusion-rate limiting member for introducing the intake atmosphere into the measurement chamber are formed, between the oxygen pump cell and the detection cell. One electrode of the oxygen pump cell is arranged outside the measurement chamber, and the other electrode is arranged in the measurement chamber. Furthermore, one electrode of the electromotive force detection cell is arranged inside the chamber, and the other electrode is insulated by a laminated layer of the heater 17 described below from an external atmosphere, and is exposed to an oxygen concentration atmosphere that serves as a reference. Further, the sensing element 11 is driven by the drive control (an electric current-application control) by the oxygen sensor control unit 12. Specifically, the electric current-application state of pump current that is supplied to the oxygen pump cell is controlled such that an electromotive force (potential) generated by the electromotive force detection cell, based on the oxygen concentration in the measurement chamber, serves as a target value. At this time, the pump current which flows through the oxygen pump cell is output as the output signal Ip, and the output signal Ip is a signal depending on the oxygen concentration.

Furthermore, the heater 17 is laminated on the sensing element 11 on the side of the electromotive force detection cell, and is heated such that the oxygen pump cell and the electric-motive-force detection cell are activated. The heater 17 has a well-known configuration that inserts a heat-resistant element into two dielectric layers for enclosure. A main ingredient of each of the two dielectric layers is alumina.

The oxygen sensor control unit 12 performs, for example, the drive control (the electric current-application control) on the sensing element 11 and the heater 17, and constitutes the oxygen sensor 10. Furthermore, the oxygen sensor control unit 12 updates the compensation coefficient Ipcomp that is used to compensate the output signal Ip when a change occurs in the correspondence relationship between the output signal Ip output from the sensing element 11 and the oxygen concentration in the intake atmosphere. In addition, the electric current-application control of the sensing element 11 and the heater 17 by the oxygen sensor control unit 12 is performed using a well-known circuit configuration and a description of the electric current-application control is therefore omitted.

A detection unit 13 that detects the output signal Ip output from the sensing element 11, an input unit 14 to which a control signal such as an idle switch from an ECU (a determination unit) 43 is input, a calculation unit 15 that performs the compensation processing relating to the output signal Ip used in calculating the oxygen concentration, and a storage unit 16 that is a writable non-volatile memory (an EEPROM) mainly constitute the oxygen sensor control unit 12.

The detection unit 13 has a circuit for detecting the output signal Ip of the sensing element 11, and has, for example, a filter circuit removing noise and the like. The output signal Ip detected by the detection unit 13 is input to the calculation unit 15.

A control signal relating to a specific operating state, which is output from the ECU 43, and more particularly, a control signal that is output when the ECU 43 determines that the oxygen concentration in the intake atmosphere around the oxygen sensor 10 is in a specific state where the oxygen concentration in the atmosphere has been approximately considered (based on opening degree signals (state signals) output from the EGR opening-degree sensor 20 and the throttle opening-degree sensor 21 and a revolution-per-minute signal (the state signal) output from the revolution-per-minute sensor 30) is input to the input unit 14. In addition, in the present embodiment, the detection unit 13 and the input unit 14 are described, using an example in which the detection unit 13 and the input unit 14 are separately arranged. However, the detection unit 13 and the input unit 14 may be integrated as one piece into an interface unit and the configurations thereof are not particularly limited.

The calculation unit 15 is a microcomputer that has a CPU (a central processing unit), ROM, RAM, an input/output interface, and the like, and performs calculation processing such as the calculation of and update on the compensation coefficient Ipcomp relating to the output signal Ip of the sensing element 11 by executing a control program stored in the ROM. In addition, the calculation processing in the calculation unit 15 is described below.

The EGR opening-degree sensor 20 is a sensor that detects the opening degree of the EGR valve 53 and outputs the opening degree signal to the ECU 43. The throttle opening-degree sensor 21 is a sensor that detects the opening degree of the throttle valve 45 and outputs the opening degree to the ECU 43. Sensors with various measurement forms may be used as the EGR opening-degree sensor 20 and the throttle opening-degree sensor 21, and the measurement form thereof is not particularly limited.

The revolution-per-minute sensor 30 is a sensor that detects the number of revolutions of the engine 40 and outputs the revolution-per-minute signal to the ECU 43. Sensors with various measurement forms may be used as the revolution-per-minute sensor 30 EGR, and the measurement form thereof is not particularly limited.

Next, the compensation processing that updates the compensation coefficient Ipcomp from the output signal Ip of the sensing element 11 in the sensor control system 1 with the configuration described above is described with reference to FIG. 3. In addition, a method of calculating the oxygen concentration from the output signal Ip of the sensing element 11 using the compensation coefficient Ipcomp is the same as the well-known method of multiplying the output signal Ip by the compensation coefficient Ipcomp, and its description is therefore omitted.

Figure 3:
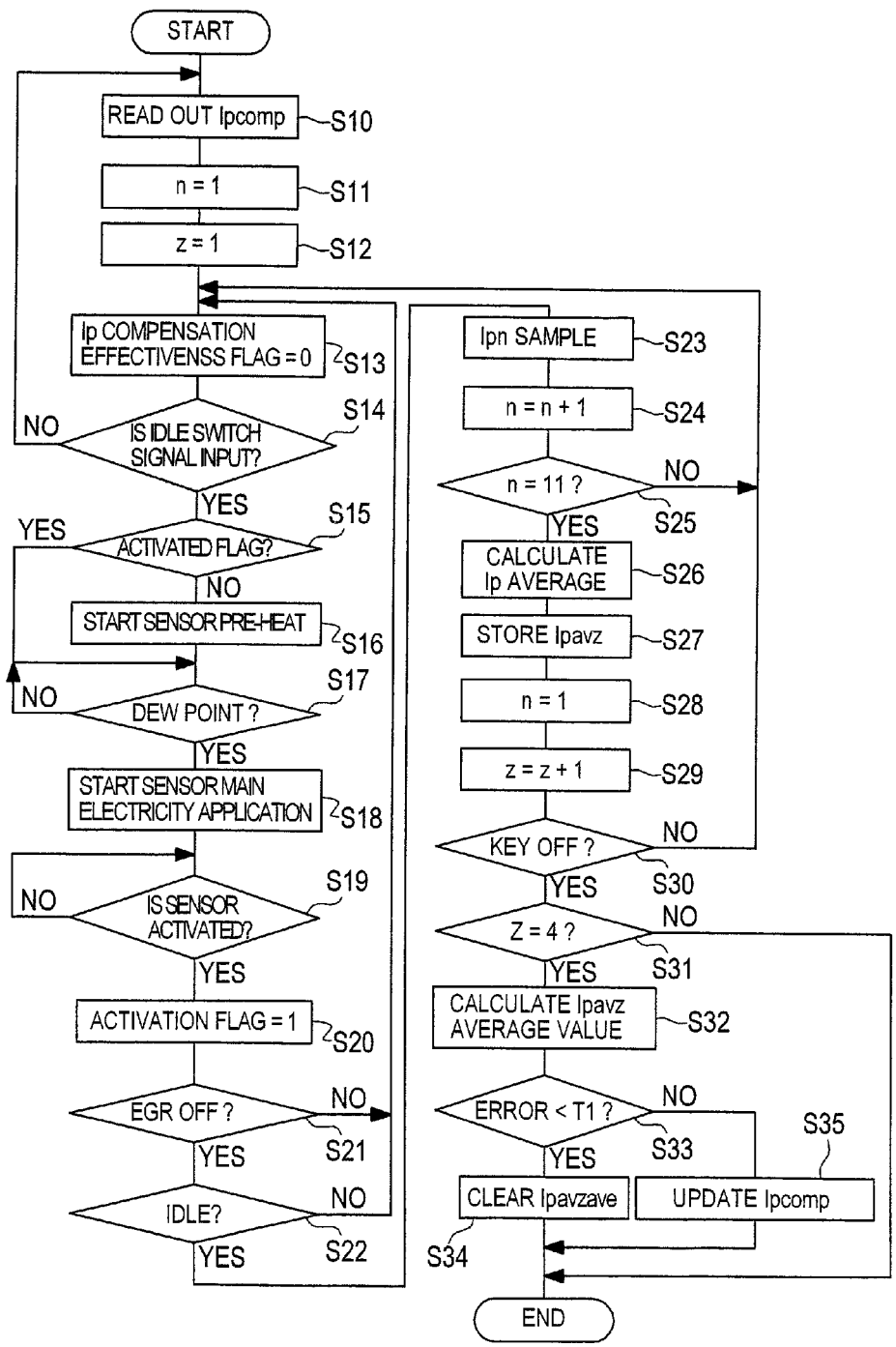
FIG. 3 is a flow chart which describes processing that compensates a compensation coefficient in the sensor control system of FIG. 1.

When electric power is supplied to the sensor control system 1 and the processing that compensates the compensation coefficient Ipcomp begins, the calculation unit 15, as illustrated as in the flow chart of FIG. 3, performs the processing that reads out the most recent compensation coefficient Ipcomp stored in the storage unit 16 of the calculation unit 15 (S10). In addition, in an initial state of the sensor control system 1, the compensation coefficient that is set in advance is stored in the storage unit 16 as the most recent compensation coefficient Ipcomp.

Subsequently, when a power supply of the calculation unit 15 is switched on, the calculation unit 15 performs processing that clears a value of a variable n of a compensation Ip sample to "1" (S11), and performs processing that resets a value of a variable z of the compensation Ip average value to "1" (S12). Moreover, the calculation unit 15 performs processing that clears a value of an activation flag, which indicates whether or not the sensing element 11 is activated, to "0" (S13).

When the initial setting processing from S11 to S13 described above ends, the calculation unit 15 performs processing that determines whether or not the idle switch signal, which is output from the ECU 43 when it is determined that the engine 40 is in an idle operation state, is input (S14). The determination in the ECU 43 of whether or not the engine 40 is in an idle operation state is performed by determining whether or not the engine 40 is in a state of revolving without outputting significant power. Specifically, the determination is made by determining whether or not any one of the following conditions is met: 1) an accelerator pedal is in an almost no-load condition without being depressed (including a state in which a vehicle is at a very low speed caused by transmission of torque to wheels via a torque converter (i.e., a creep state), 2) an internal combustion engine is in a warming-up operation state, and 3) a gear shift lever of a vehicle is in a neutral state. In addition, the determination may be made by determining whether or not the operation state of the engine 40 is at a low revolution-per-minute state or a low-load condition. Specifically, whether or not the operation state of the engine 40 is at a low revolution-per-minute state may be determined based on the revolution-per-minute signal input from the revolution-per-minute sensor 30, and whether or not the operation state of the engine 40 is at a low-load condition may be determined based on the throttle opening-degree signal input from the throttle opening-degree sensor 21.

In the determination in S14, in a case where it is determined that the idle switch signal is not input (in a case of NO), the calculation unit 15 returns to S10 described above and repeats the calculation processing described above.

On the other hand, in a case where a determination is made that the idle switch signal is input (in the case of YES), the calculation unit 15 performs processing that determines whether or not the sensing element 11 is activated (S15). That is, processing is performed that determines whether the value of an activation flag is "0" indicating that the sensing element 11 is not activated, or "1" indicating that the sensing element 11 is activated.

When a determination is made that the sensing element 11 is not activated (in a case of NO), the calculation unit 15 performs a sensor pre-heating control processing with respect to the heater 17 heating the sensing element 11 (S16). Specifically, the electric current-application control processing is performed on the heater 17 that heats the sensing element 11 to a temperature at which the sensing element 11 is not broken even though water adheres thereto, and maintains that temperature.

After performing the sensor pre-heating control processing, or in the determination processing in S15, the calculation unit 15 performs the processing that determines whether or not the temperature of the sensing element 11 exceeds a dew point in a case where a determination is made that the sensing element 11 is activated (in the case of YES) (S17). The calculation unit 15 returns to S17 and repeats the processing that determines whether or not the temperature of the sensing element 11 exceeds the dew point in the case where a determination is made that the temperature of the sensing element 11 does not exceed the dew point (in the case of NO). In other words, the determination processing in S17 is repeated until the temperature of the sensing element 11 exceeds the dew point.

The calculation unit 15 performs the sensor main electric current-application processing with respect to the heater 17 in the case where a determination is made that the temperature of the sensing element 11 exceeds the dew point (S18). The sensor main electric current-application processing is the processing that PWM (pulse width modulation) controls electric power that is supplied to the heater 17, so that the impedance of the sensing element 11 (particularly, the impedance of the electromotive force detection cell) is a target impedance stored in advance. In other words, the sensor main electric current-application processing is the processing that controls the electric power supplied to the heater 17, so that the temperature of the sensing element 11 reaches a target temperature defined in advance.

When the sensor main electric current-application processing begins, the calculation unit 15 performs the processing that determines whether or not the sensing element 11 is activated (S19). Specifically, a determination of whether or not the sensing element 11 is activated is made by comparing the impedance of the sensing element 11 (the electromotive force detection cell) and a threshold value relating to the activation, stored in advance. In addition, a well-known technique may be adopted which detects the impedance of the sensing element 11 (the electromotive force detection cell) based on a change in voltage that is detected when a constant value of a change in the electric current is supplied to the electromotive force detection cell. In the determination processing in S19, in a case where a determination is made that the sensing element 11 is not activated (in the case of NO), the calculation unit 15 returns to S19 described above and repeatedly performs the processing that determines whether or not the sensing element 11 is activated.

In the determination processing in S19, in a case where a determination is made that the sensing element 11 is activated (in the case of YES), the calculation unit 15 performs processing that sets a value of the activation flag to "1" indicating that the sensing element 11 is activated (S20). In other words, processing is performed that enables the calculation unit 15 to recognize an activation experience of the sensing element 11.

Subsequently, the calculation unit 15 performs processing that determines whether or not the sufficient time has passed after the EGR device 50 has been powered off (S21). In other words, a process is performed that determines whether or not the time for the concentration of the exhaust gas in the intake atmosphere flowing around the oxygen sensor 10 to stabilize has passed after the EGR valve 53 of the EGR device 50 is closed. Specifically, the calculation unit 15 determines whether or not the EGR device 50 has been powered off, based on the opening degree signal input from the EGR opening-degree sensor 20. Moreover, the time that has passed after the EGR device 50 has been powered off is measured, and processing is performed that determines whether or not the time that has passed is a sufficient time. In the determination processing in S21, in a case where a determination is made that sufficient time has not passed (in the case of NO), the calculation unit 15 returns to S13 described above and repeatedly performs the processing described above.

In the determination processing in S21, in a case where a determination has been made that a sufficient time has passed (in the case of YES), the calculation unit 15 performs processing that determines whether or not the idle operation state of the engine 40 continues for a predetermined period (S22). In other words, processing is performed that determines whether or not the time needed for the pressure and flow velocity of the intake atmosphere around the oxygen sensor 10 to stabilize has passed. Specifically, the calculation unit 15 performs processing that either determines (i) whether or not the period during which the idle switch signal from the ECU 43 is input continues for a predetermined period, or (ii) whether or not the time that has passed after the idle switch signal was input has reached a predetermined period. In the determination processing in S22, in the case where a determination is made that the idle operation state does not continue for the predetermined period (in the case of NO), the calculation unit 15 returns to S13 described above and repeatedly performs the processing described above.

In the determination processing in S22, in a case a determination is made that the idle operation state has continued for the predetermined period (in the case of YES), the calculation unit 15 performs processing that acquires an Ipn sample (compensation information) that is the output signal Ip used in the calculation of the compensation coefficient (S23). The output signal Ip acquired as the Ipn sample is the output signal Ip output from the sensing element 11, also called a "fresh signal". Specifically, the acquired output Ip is stored as the Ipn sample in the storage unit 16.

Subsequently, the calculation unit 15 performs processing that updates the value of a variable n of the compensation Ipn sample (S24). Specifically, processing is performed that increases the value of the variable n by a value of one at a time. When the value of variable n is updated, the calculation unit 15 performs processing that determines whether or not the value of the variable n has reached 11 (S25). In other words, processing is performed that determines whether or not the number of times that the compensation Ipn sample is acquired has reached 10. In a case where n has not reached 11 (in the case of NO), the calculation unit 15 returns to S13 described above, and repeatedly performs the processing described above.

In the case where n has reached 11 (in the case of YES), the calculation unit 15 performs processing that acquires Ipavz, which is an average value of the Ipn samples, by the calculation (S26). Specifically, the average value Ipavz is calculated by processing that averages the most recent ten Ipn valves stored in the storage unit 16 (an arithmetic average processing).

The calculation unit 15 stores the calculated average value Ipavz in the storage unit 16 (S27). Subsequently, the calculation unit 15 performs processing that resets the value of the variable n of the compensation Ip sample to "1" (S28), and performs processing that updates the variable z of the compensation Ip average value (S29). In other words, processing is performed that increases the value of the variable z by a value of one at a time.

Subsequently, the calculation unit 15 performs processing that determines whether or not a key-OFF signal output from the ECU 43 when a determination is made that an ignition key is in an OFF position is input (S30). In the case where a determination is made that the key-OFF signal is not input (in the case of NO), the calculation unit 15 returns to S13 described above and repeatedly performs the processing described above.

In the case where a determination is made that the key-OFF signal is input (in the case of YES), the calculation unit 15 begins processing that updates the value of the compensation coefficient Ipcomp. First, the calculation unit 15 performs processing that determines whether or not the value of the variable z reaches 4 (S31). In other words, processing is performed that determines whether or not the number of times that the average value Ipavz stored in the storage unit 16 is calculated (acquired) reaches 3. In the case where z in the variable z has not reached 4 (in the case of NO), the calculation unit 15 ends this compensation processing, without performing the processing that updates the compensation coefficient Ipcomp. On the other hand, in the case where z in the variable z reaches 4 (in the case of YES), calculation processing is performed that reads out the most recent three average values Ipavz from the storage unit 16 and acquires the average value Ipavzave that is a result of average processing (arithmetic average processing) of the average values Ipavz (S32).

When the average value Ipavzave is calculated, the calculation unit 15 performs processing that determines whether or not an error that is a difference (an absolute value of the difference) between the value that is a result of multiplying the average value Ipavzave by the compensation coefficient Ipcomp and the value of the oxygen concentration (the basic value) stored in advance in the calculation unit 15 is within a predetermined range (less than T1) of predetermined values (S33). In the case where the error described above is within the predetermined range (less than T1) (in the case of YES), the calculation unit 15 performs processing that clears the value of the average value Ipavzave to "0" (S34).

In the case where the error described above is out of the predetermined range (T1 or more) (in the case of NO), the calculation unit 15 performs processing that updates the value of the compensation coefficient Ipcomp that has been used until that time (S35). Specifically, processing is performed that calculates a new compensation coefficient Ipcomp by dividing the basic value stored in advance in the calculation unit 15 by the average value Ipavzave, and processing is performed that stores (updates) the new compensation coefficient Ipcomp, as the compensation coefficient Ipcomp to be used thereafter, in the storage unit 16. As described above, the processing is completed once compensation of the compensation coefficient Ipcomp in the sensor control system 1 is completed.

According to the sensor control system 1 equipped with the oxygen sensor control unit 12 with the configuration described above, calculation of the compensation coefficient Ipcomp is performed based on the Ipn sample that is collected when the operation state of the engine 40 is a state that is in operation and is a state in which the oxygen concentration in the intake atmosphere may be estimated (when a positive determination is made in each of S21 and S22). Because of this, even though a deviation may occur due to deterioration in the sensing element 11, in a correspondence relationship between the value of the output signal of the sensing element 11 and the oxygen concentration in the intake atmosphere, the deviation in the corresponding correspondence relationship may be resolved. This is achieved by performing the processing that compensates the output signal Ip using the compensation coefficient Ipcomp calculated in the calculation unit 15.

An Ipn sample of high accuracy may be collected by changing the specific state that may estimate the oxygen concentration in the intake atmosphere to a state in which the EGR valve 53 of the EGR device 50 is closed.

That is, the state in which the EGR valve 53 is closed is a state in which exhaust gas recirculating in the intake atmosphere is not present. In other words, the oxygen concentration in the intake atmosphere is in such a state that may be estimated to be the same as the oxygen concentration in the atmosphere. Because of this, the oxygen concentration in the intake atmosphere in the state where the EGR valve 53 is closed may be determined with high accuracy and an Ipn sample of high accuracy may be collected.

Furthermore, an Ipn sample of high accuracy may be collected by changing the specific state in which the oxygen concentration in the intake atmosphere may be estimated, to an operation state in which the engine 40 is at idle.

That is, in a case where the engine 40 is in idle operation, a flow volume of the intake atmosphere to the engine 40 is decreased, as compared to the case in which the engine 40 is in operation in a high-load condition. Then, in a position where the sensing element 11 is located, a flow velocity of the intake atmosphere is decreased and a pressure of the intake atmosphere is close to the atmospheric pressure. Generally, the output signal Ip is an output from the sensing element 11 that depends on the sensing element temperature, and further depends on the surrounding pressure. An amount of heat of the sensing element 11 removed by the intake atmosphere is decreased, by decreasing the flow velocity of the intake atmosphere. Consequently, the temperature of the sensing element 11 is readily controlled to a predetermined constant temperature, and the output signal Ip is easy to stabilize. Similarly, by controlling the pressure around the sensing element 11 to a predetermined constant pressure, that is, to approximately the atmospheric pressure, the output signal Ip is readily stabilized. Thus, a more accurate compensation may be performed by stabilizing the output signal Ip and then collecting the Ipn sample.

Moreover, the case where the engine 40 is in idle operation is the case where a load applied to the engine 40 is small, and is the case where the amount of blow-by gas is small. When the blow-by gas mixes into the intake atmosphere, this becomes a source of error that occurs when estimating the oxygen concentration in the intake atmosphere. By collecting the Ipn sample when the engine 40 is in idle operation, the influence of blow-by gas is small. Consequently, a compensation coefficient Ipcomp of high accuracy may be calculated, for example, as compared to the case where the Ipn sample is collected when the engine 40 operates under a high-load condition.

Moreover, the time for the state of the intake atmosphere of the engine 40 to reach an equilibrium state is shortened. This is because the calculation unit 15 collects the Ipn sample when the engine 40 is in operation, as compared to the case where the Ipn sample is collected while the engine 40 is stopped. Because of this, the time needed to calculate the compensation coefficient Ipcomp in the calculation unit 15 may be shortened, and consumption of the electric power of a battery may be suppressed. Moreover, consumption of the electric power of the battery may be suppressed because the Ipn sample is collected while a generator is driven by the engine 40, and the battery installed together with the engine 40 is charged, as compared to the case where the Ipn sample is collected while the engine 40 is stopped.

By performing processing that updates the compensation coefficient Ipcomp only in the case where the difference between the value of the oxygen concentration stored in advance in the calculation unit 15 and the value obtained as a result of multiplying the average value Ipavzave by the compensation coefficient Ipcomp is out of the predetermined range (T1 or more), a risk of reducing the accuracy in measuring the oxygen concentration is decreased as compared to the case where excessive updates of the compensation coefficient Ipcomp are performed.

Moreover, as in the embodiment described above, the case where the EGR valve 53 of the EGR device 50 is closed may be used as the case where the oxygen concentration in the intake atmosphere may be estimated. Also, the opening degree of the EGR valve 53 may be in a state of less than a predetermined opening degree in which the oxygen concentration stored in advance in the calculation unit 15 and the oxygen concentration in the intake atmosphere are considered to match each other.

Moreover, in the embodiment, the compensation coefficient Ipcomp is described, using an example in which processing that updates the value of the compensation coefficient Ipcomp begins, after the key-OFF signal is input to the calculation unit 15, in other words, after the engine 40 is stopped. However, the processing that updates the value of the compensation coefficient Ipcomp may begin while the engine 40 is in operation. That is, the Ipn sample is necessarily collected to calculate the compensation coefficient Ipcomp while the engine 40 is in operation. However, the timing of the processing that calculates the compensation coefficient Ipcomp using the Ipn sample (the average value Ipavzave) is not particularly limited in the present embodiment.

Figure 4:
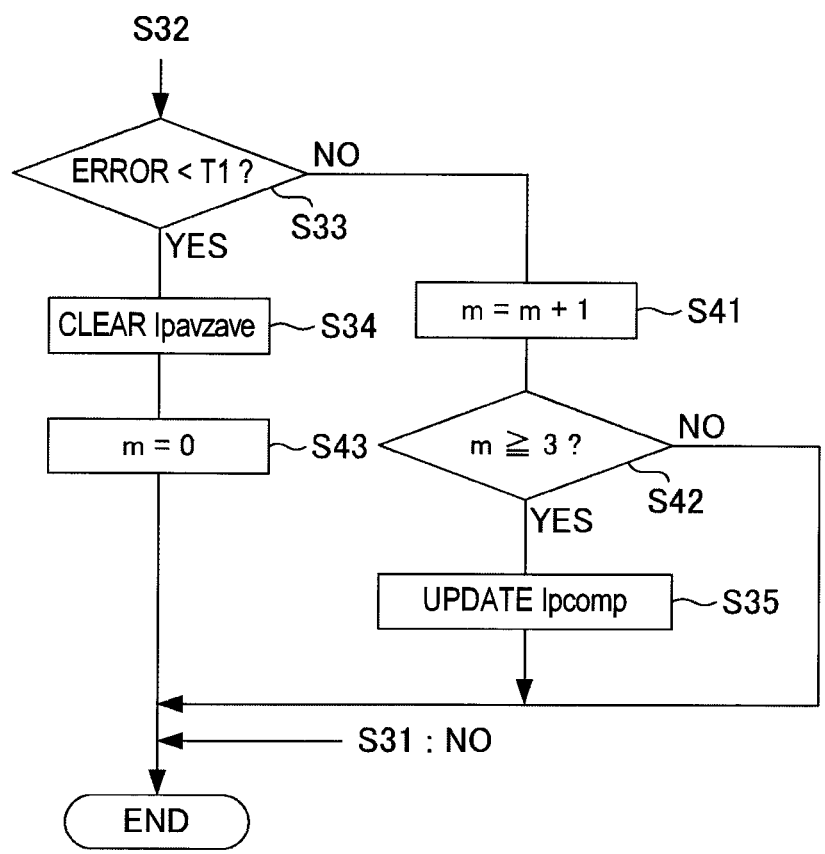
FIG. 4 is an essential section of the flow chart which describes another embodiment in the processing that compensates the compensation coefficient.

Moreover, as in the embodiment described above, the processing that updates the value of the compensation coefficient Ipcomp may be performed based on a one-time determination result in S33 (S35). As illustrated as the flow chart of FIG. 4, the processing that updates the value of the compensation coefficient Ipcomp may be performed for the first time after the determination result in S33 turns out three times to be NO. Specifically, in a case where the determination result in S33 turns out to be NO, the processing that counts the number m of times that the determination result turns out to be NO is performed (S41). Thereafter, processing is performed to determine whether or not the number of times that the determination result turns out to be NO is three or more (S42). In a case where the number m of times that the determination result turns out to be NO is three or more, processing is performed that updates the value of the compensation coefficient Ipcomp. In a case where the number m of times that the determination unit turns out to be NO is less than three, the compensation processing ends, and the next compensation processing begins.

Furthermore, in the case where the determination result in S33 turns out to be YES, processing is performed that clears the value of the average value Ipavzave to "0" (S34), and then the processing performed that clears the number m of times that the determination result in S33 turns out to be NO to "0" (S43). In this manner, the processing that updates the value of the compensation coefficient Ipcomp may be suppressed, which is caused by an erroneous determination.

Second Embodiment

Next, a sensor control system according to a second embodiment of the present invention is described by reference to FIG. 5. A basic configuration of the sensor control system of the present embodiment is the same as that of the first embodiment, but is different from the first embodiment with respect to the position where the oxygen sensor control unit is arranged. Therefore, in the present embodiment, the position of the oxygen sensor control unit is described by reference to FIG. 5, and the description of other parts are omitted.

Figure 5:
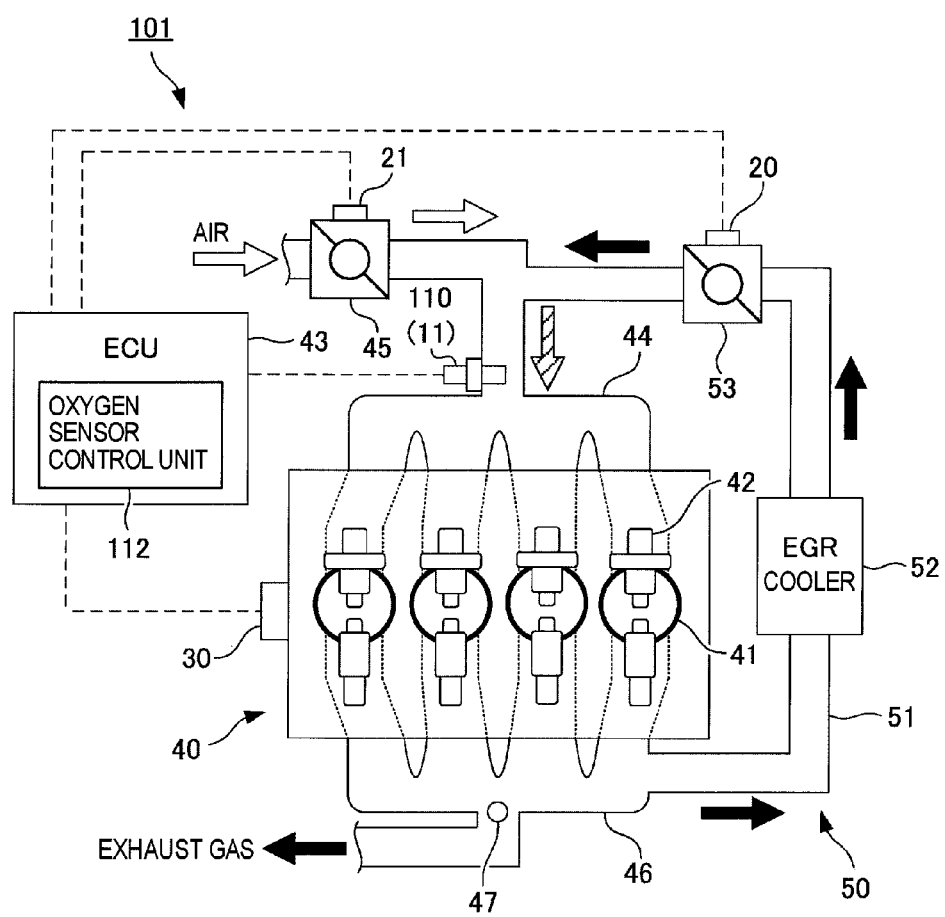
FIG. 5 is a schematic diagram of the entire configuration of a sensor control system according to a second embodiment of the present embodiment.

As illustrated in FIG. 5, an oxygen sensor 110 equipped with a sensing element 11 measuring the oxygen concentration in the intake atmosphere and a heater 17, an EGR opening-degree sensor 20 detecting an opening degree of an EGR valve 53 of an EGR device 50, a throttle opening-degree sensor 21, a revolution-per-minute sensor 30 detecting the number of revolutions of an engine 40, and an oxygen sensor control unit (an oxygen sensor device) 112 compensating an output signal Ip output from the sensing element 11 mainly constitute the sensor control system 101.

That is, the present embodiment is different from the first embodiment in which the sensing element 11 and the oxygen sensor control unit 12 are provided in the oxygen sensor 10, in that the oxygen sensor control unit 112 is not provided in the oxygen sensor 110 in the present embodiment. In the present embodiment, the oxygen sensor control unit 112 is described, using an example in which the oxygen sensor control unit 112 is arranged in an ECU 43 controlling the engine 40.

The oxygen sensor control unit 112 collects an Ipn sample while the engine 40 is in operation, the same as the oxygen sensor control unit 12 of the first embodiment. Furthermore, the oxygen sensor control unit 112 performs processing that compensates a compensation coefficient Ipcomp and enables oxygen concentration to be accurately calculated. The sensing element 11, a detection unit 13 detecting an output signal Ip in addition to making up a circuit performing drive control (electric current-application control) of the heater 17, an input unit 14, a calculation unit 15 performing compensation processing relating to the output signal Ip, and a storage unit 16 mainly constitute the oxygen sensor control unit 112 (refer to FIG. 2).

The processing that compensates the compensation coefficient Ipcomp in the sensor control system 101 with the configuration described above is the same as the compensation processing in the sensor control system 1 according to the first embodiment and thus a description thereof is omitted.

The invention has been described in detail with reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

This application is based on Japanese Patent Application No. 2011-251701, filed Nov. 17, 2011, and Japanese Patent Application No. 2012-217061, filed Sep. 28, 2012, incorporated herein by reference in its entirety.

What is claimed is:

1. A sensor control device for connection to an oxygen sensor including a sensing element that measures oxygen concentration in an intake atmosphere of an internal combustion engine and a heater that heats the sensing element, the sensor control device comprising:
    a detection unit that detects an output signal corresponding to the oxygen concentration output from the sensing element; and
    a calculation unit that calculates a compensation coefficient of the output signal used for calculating the oxygen concentration,
    wherein the calculation unit collects compensation information used in calculating the compensation coefficient when the internal combustion engine is in operation and in a specific operation state in which the oxygen concentration in the intake atmosphere is subject to estimation,
    the specific operation state is a state in which an opening degree of a control valve controlling an amount of recirculating exhaust gas, which is provided in an exhaust gas recirculation device that recirculates a part of the exhaust gas in the internal combustion engine into the intake atmosphere, is less than a predetermined opening degree and the internal combustion engine is in an idle state, an oxygen concentration in the intake atmosphere in a case where the opening degree of the control valve is less than the predetermined opening degree and the internal combustion engine is in the idle state is stored in advance in the calculation unit, the calculation unit collects the compensation information when the opening degree of the control valve is less than the predetermined opening degree and when the idle state has continued for a predetermined period of time, the calculation unit determines whether an ignition key for the internal combustion engine is in an off position, and the calculation unit calculates and updates the composition coefficient when the ignition key is in the off position.

2. The sensor control device as claimed in claim 1,
wherein the oxygen concentration in the operation state where the opening degree of the control valve stored in advance in the calculation unit is less than the predetermined opening degree is the oxygen concentration in the intake atmosphere when the control valve is closed, and wherein the calculation unit collects the compensation information when the control valve is closed.

3. The sensor control device as claimed in claim 1,
wherein a basic value that is the output signal of the sensing element with respect to the oxygen concentration in the specific operation state is stored in advance in the calculation unit, and wherein the calculation unit stores a plurality of the output signals detected in the specific state, calculates an average value of the plurality of the stored output signals, and updates the compensation coefficient in a case where a difference between the basic value stored in advance and the average value is greater than a predetermined value.

4. A sensor control system comprising:
an oxygen sensor including: a sensing element that measures oxygen concentration in an intake atmosphere in an internal combustion engine, and a heater heating the sensing element;

a state measurement unit that outputs a state signal corresponding to an operation state of the internal combustion engine;

a determination unit that determines whether or not the internal combustion engine is in a specific operation state, based on the state signal; and the sensor control device as claimed in claim 1,
wherein the calculation unit of the sensor control device collects the compensation information based on a determination result by the determination unit.

* * * * *